United States Patent [19]
Ruefer

[11] Patent Number: 5,480,711
[45] Date of Patent: Jan. 2, 1996

[54] NANO-POROUS PTFE BIOMATERIAL

[76] Inventor: Bruce G. Ruefer, 3305 66th St., Lubbock, Tex. 79413

[21] Appl. No.: 273,460
[22] Filed: Jul. 12, 1994
[51] Int. Cl.$^6$ ................................................... H01B 7/18
[52] U.S. Cl. ................................ 428/315.5; 428/315.7; 428/316.6; 428/318.4; 428/421; 428/422; 428/304.4
[58] Field of Search .................................... 428/131, 421, 428/422, 315.5, 316.6, 318.4, 304.4

[56] References Cited
U.S. PATENT DOCUMENTS 4,187,390  2/1980  Gore .......................................... 174/102
4,819,478  4/1989  Melcher ..................................... 73/61.1
4,849,285  7/1989  Dillon ........................................ 428/330
4,859,383  8/1989  Dillon ........................................ 264/43
5,194,154  3/1993  Moyer et al. ............................ 210/510.1

Primary Examiner—James J. Bell
Assistant Examiner—Helen F. Lee

[57] ABSTRACT

The invention provides for a nano-porous highly amorphous polytetrafluoroethylene biomaterial which is soft, flexible, permeable to various biomolecules and gases, and high in strength in one or more directions. The invention can be made into many desired shapes as product needs dictate and multidirectional strength can be attained by layering the invention.

6 Claims, 3 Drawing Sheets

NANO-POROUS PTFE BIOMATERIAL

BACKGROUND OF THE INVENTION

In the area of biomaterials design, two major material characteristics are noted to be of importance. These are the chemical and the mechanical properties of the biomaterial. Chemical properties dictate whether a biomaterial is toxic, carcinogenic, reactive, or degradable within the bio-system. Mechanical properties determine a biomaterial's capabilities as a load-bearing device, tissue augmentation device, or tissue replacement device. It is generally known that the flexure properties of a biomaterial must match closely that of juxtaposed tissue in order for long term implant success to occur. Stiff or rigid implant material joined to softer tissues will cause immediate tissue response including encapsulation of the implant. Of additional importance are the density of the biomaterial, the porosity of the biomaterial, the creep resistance of the biomaterial, and the elasticity characteristics of the biomaterial. Relative porosity allowing permeability of the biomaterial to biomolecules such as albumin, fibrinogen, lipoprotein, and macroglobulin is also important for the long term success of the biomaterial.

Following implantation of most biomaterials, the immediate response of a bio-system, such as the human body, is to expel the biomaterial. Biomaterials can either be extruded from the body or walled-off if the materials cannot be removed. These responses are related to the healing process of the wound where the biomaterial is present as an additional factor. A typical response is that inflammation-activating leukocytes quickly appear near the biomaterial followed by giant cells which try to engulf the material. If the biomaterial is inert enough, foreign body giant cells may not appear near the biomaterial, lowering the overall inflammatory response.

Silicone polymers continue to be used commercially as biomaterials in both short-term and long-term implant devices. The relative chemical inertness of silicone makes it a fairly non-toxic biomaterial for long term implantation with relatively few complications reported. The elastic mechanical property of the silicone polymer allows the material to be used in load bearing applications without appreciable problems of material creep or tearing. While permeable to certain gases such as oxygen and carbon dioxide, silicone polymers are relatively impermeable to biological proteins, fluids or cells.

Open-structure, highly-crystalline porous materials such as micro-porous expanded polytetrafluoroethlyene or ePTFE are used as biomaterials to manufacture medical devices as well. Vascular grafts, soft tissue patches, sutures, ligaments, tissue augmentation membranes, and burn membranes are such devices made of ePTFE. The chemical inertness or non-reactive nature of polytetrafluoroethylene provides for a very non-toxic biomaterial. Expanded PTFE is characterized by its low density of typically less than 1 gm/cc, its high crystallinity, and its fibril and node open structure of average pore size typically greater than 30 micrometers. Implant products made of micro-porous ePTFE are typically designed to allow for cellular infiltration or tissue ingrowth during implantation. While cellular ingrowth is sometimes desirable, complications may result. These complications include but are not limited to infection, increase in implant rigidity leading to tissue compliance problems, and difficulty in removing the implant should the need arise. In addition, the highly crystalline nature of ePTFE presents mechanical compliance problems in many biomaterial applications due to the inherent stiffness of ePTFE medical devices.

BRIEF DESCRIPTION OF THE INVENTION

The invention described herein is a highly-amorphous soft and flexible nano-porous polytetrafluoroethylene or nPTFE material that is molecularly porous to biomolecules and gases. The invention provides biomaterial products which demonstrate excellent biocompatibility and tissue compliance. The preferred invention is characterized by a relatively high density from about 1.2 gm/cc to about 2.0 gm/cc, a high amorphous or non-crystalline content, and a nano-porosity from about 5 nanometers to about 5,000 nanometers to about 5,000 nanometers.

DETAILED DESCRIPTION OF THE INVENTION

The goal of this invention is to provide a non-toxic soft and flexible biomaterial that is preferentially porous to certain biomolecules and gases while excluding cellular components such as blood cells and fibroblasts. In addition, this invention is soft and compliant such that biocompatibility is enhanced due to better tissue compliance match. This goal is accomplished firstly by a process involving extrusion of resin-paste. Polytetrafluoroethylene resin is mixed with an extrusion-aid such as mineral spirits and compressed at relatively low pressures into an extrusion pellet. The pellet is then extruded at slow rates in a ram extruder. In this device, the ram serves mainly to further compact the resin and extrusion-aid paste and feed it into a die. The resin extrusion aid paste is subjected to very high pressure and shear forces within the die such that the resin solidifies into a cohesive shaped article.

The high pressure and shearing action within the die tends to align the high-molecular weight polytetrafluoroethylene chains along the longitudinal axis of the extrudate such that longitudinal strength is greatly enhanced and transverse strength is noticeably lowered. This extruded strength-orientated material is the precursor to the invention herein.

The preferred invention utilizes the extruded strength-orientated material described in the paragraph above. When this strength-orientated material is formed and compressed by multiple passes through a calender device at slow rates and high pressure, the aligned polytetrafluoroethylene chains separate one from another in a parallel or semi-parallel fashion. This separation process provides openings or voids of various dimensions between the polymer chains. The structure provided by this chain separation provides significant space for passage of biomolecules and gases. Increases in average intermolecular chain distance are dependent on the amount of compression, the rate of compression, the orientation of polymer chains relative to the direction of calender compression, the temperature of the material, the number of passes through the calender device, and the amount of lubricant within the material during the calender process. Lubricant is removed from the invention by drying at a temperature slightly above the boiling point of the lubricant, generally at about 150° C., and far below the sintering or coalescing temperature of the polymer, generally at about 327° C. The relatively low temperature drying process prevents the preferred invention from coalescing into a rigid, very high-density polytetrafluoroethylene material with a density of about 2.2 gm/cc and a nature of highly crystalline non-porous structure.

The nano-porous structure of the invention consists of separated chains of amorphous polytetrafluoroethylene with average interchain distances from about 50 nanometers to about 5,000 nanometers or 5 microns. Longitudinal strength along the chain-orientation is about 500 pounds per square inch or psi and transverse strength is about 250 psi. Both nano-porosity and strength can be significantly affected by the calendering process. A process of high pressure and large number of passes through the calender device typically results in greater interchain distances and highly orientated material strengths. Higher strengths are also possible and are dependent on the type of polytetrafluoroethylene resin used and the amount of lubricant used in the extrusion process. By controlling the extrusion and calendering process steps, it is possible to produce any desired nPTFE material comprised of a desired structure specific for a particular biomaterial product.

In certain biomaterial applications, it is desirable to provide a material that exhibits highly orientated strength in more than one direction. The invention can be manufactured according to the following methods to accomplish this goal. Firstly, for bi-directional strength, two extruded materials are layered such that their strength-orientation is 90° relative to one another. This layered assembly is then calendered with high pressure and multiple passes until a desired final thickness is attained. Chain separation is accomplished as described before. The final strength of the nPTFE invention is enhanced in two directions along the orientations of the two strength-orientated extruded materials. Secondly, for multi-directional strength, three or more strength-orientated extruded materials are layered such that their strength-orientations are directed in three or more directions relative one to another. This layered assembly is then calendered with high pressure and multiple passes until a desired final thickness is attained. Chain separation is accomplished as described before. The final strength of the nPTFE invention is enhanced in multiple directions along the strength-orientations of the extruded materials. An important result of the multi-layered calendar process of high pressure and multiple passes is that the layers of extruded material will be forced together such that the layers will not separate easily.

BRIEF DESCRIPTIONS OF THE DRAWINGS

DETAILED DESCRIPTIONS OF THE DRAWINGS

Figure 1:
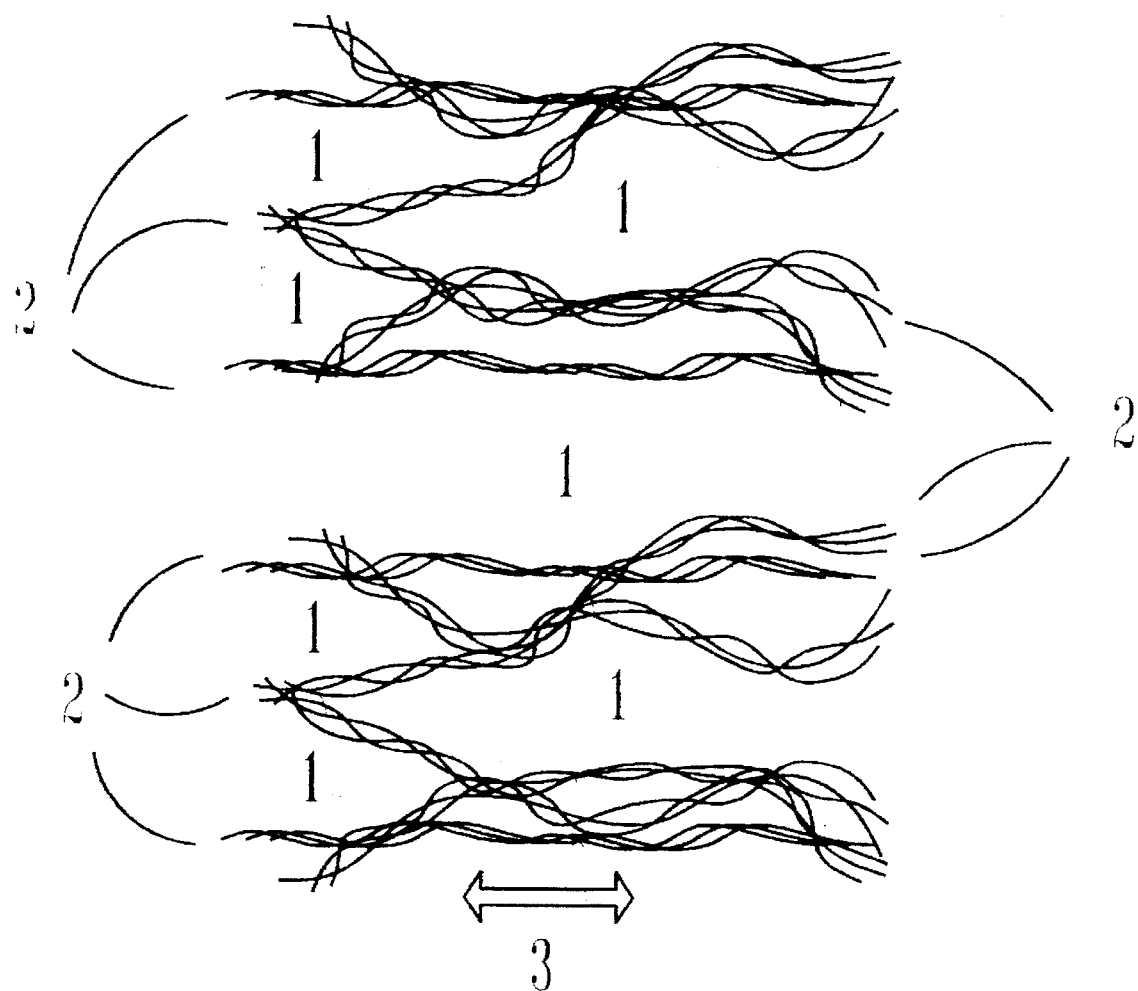
FIG. 1 is a three dimensional view of the preferred invention depicting chain separation and direction of strength.

As shown in FIG. 1, the nPTFE invention is characterized by nano-porosity formed by parallel voids 1 in the structure created by separated polymeric chains 2 of polytetrafluoroethylene. The direction of high strength is along the longitudinal orientation 3.

Figure 2:
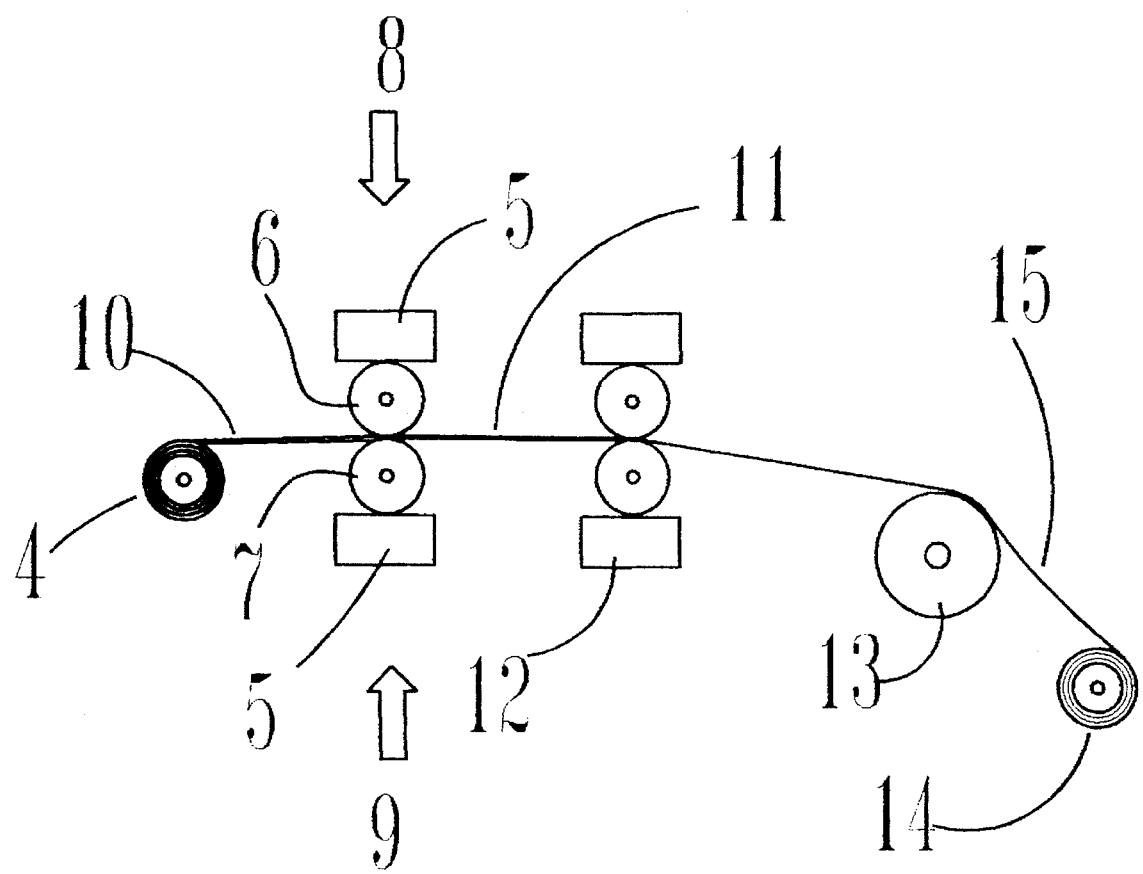
FIG. 2 is a schematic of an apparatus that may be used to manufacture the invention.

FIG. 2 describes a typical apparatus configuration for the continuous manufacture of the invention. Extruded material 4 is unrolled into an initial calender device 5 consisting of rollers 6,7 held in place with high forces 8,9. High pressure is applied to the extruded material as the thickness of the extruded material 10 is greater than the distance between the rollers 6,7. The thinner calendered material 11 passes from the first calender device 5 to the second device 12 that further processes the material. It is important to note that many more calender devices may be incorporated into the apparatus configuration to obtain the desired number of passes, pressure, thickness, and size distribution of the nano-porous voids. A drying roller 13 applies low heat to the nano-porous material to remove extrusion aid. A final take-up reel 14 stores the invention 15.

Figure 3:
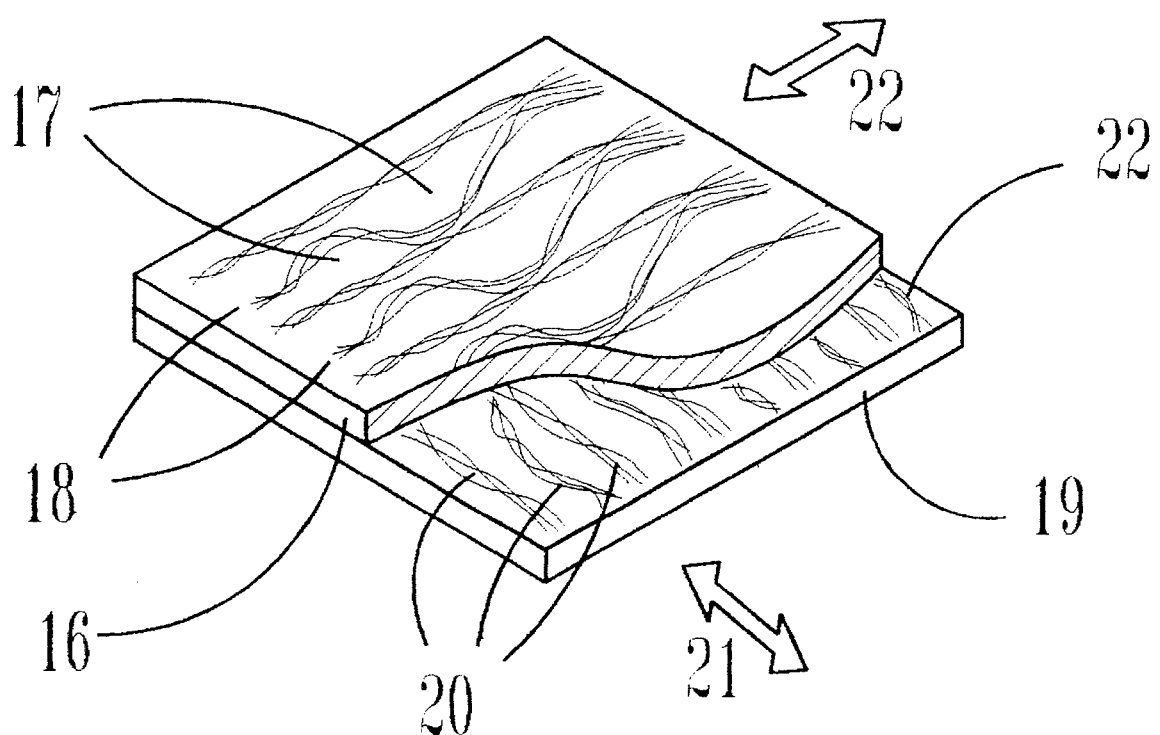
FIG. 3 is a sectional view of the multilayered invention depicting chain separation and directions of strength.

FIG. 3 shows the invention as a bi-layered nPTFE material. The top layer 16 is characterized by molecular porosity formed by parallel to semi-parallel voids 17 created by separated polymeric chains 18 of polytetrafluoroethylene. The bottom layer 19 is characterized by similar chains 20 that are at 90° orientation to chains in the top layer 16. Strength is aligned in two directions 21,22 along the orientation of the polymer chains 18,20.

EXAMPLE 1

Low Porosity Highly Amorphous nPTFE Biomaterial

Polytetrafluoroethylene resin was mixed with extrusion aid and made into a paste. The paste was made into a pre-extrusion pellet with a ram pelletizer. The pellet was then extruded with high pressure though a die to form a highly chain-orientated, flat extrudate tape of about 2 mm thickness. The extrudate tape was then calendered by multi-passes through a calender device to a final material thickness of about 0.05 mm with a reduction in thickness of about 40 to 1. Orientation of the polytetrafluoroethylene chains was maintained at 90° relative to the calender roller axes during all of the passes. The final biomaterial was then dried at about 150° C. for about 1 hour, a process that removed all of the extrusion aid. The lower density of the final 0.05 mm biomaterial was about 1.2 gm/cc as compared to the initial about 1.7 gm/cc extrudate tape. The nPTFE biomaterial was very supple and flexible indicating a non-crystalline or highly amorphous material.

The 0.05 mm nPTFE biomaterial was manufactured into a medical packing device configured such that an internal sponge component of the device was sealed within the nPTFE biomaterial. It was found that the device was water tight due to the strong hydrophobic nature of the polytetrafluoroethylene. The nPTFE packing device was then implanted for about 2 weeks in the human mastoid cavity following a radical mastoidectomy. Upon removal from the cavity, the nPTFE packing device was found to contain biological proteins and fluids soaked into the sealed sponge material such that the weight of the retrieved packing was about 6 times the original weight of the original packing. The nPTFE biomaterial itself was filled with significant amounts of biomolecules including the important blood plasma proteins albumin, lipoprotein, fibrinogen, and macroglobulin. Cells did not permeate the nPTFE biomaterial. The nano-porosity voids from about 50 nanometers to about 5,000 nanometers of the PTFE biomaterial allowed passage of the biomolecules while excluding cells, including red and white blood cells, according to TABLE I.

TABLE I

| Biomaterial | Overall Dimensions (nanometers) | Result |
| --- | --- | --- |
| Human Albumin | about 4 × 15 | permeated the nPTFE |
| Fibrinogen | about 10 × 50 | permeated the nPTFE |
| Lipoprotein | about 10 × 25 | permeated the nPTFE |
| Macroglobulin | about 20 × 50 | permeated the nPTFE |
| Red Blood Cells | about 2,000 × 8,000 | excluded by nPTFE |

TABLE I-continued

| Biomaterial | Overall Dimensions (nanometers) | Result |
| --- | --- | --- |
| Granulocytes | about 10,000 × 12,000 | excluded by nPTFE |
| Lymphocytes | about 5,000 × 8,000 | excluded by nPTFE |
| Monocutes | about 9,000 × 15,000 | excluded by nPTFE |
| Platelets | disk diameter about 4,000 | excluded by nPTFE |

What is claimed is:

1. A nano-porous PTFE biomaterial consisting of highly amorphous polytetrafluoroethylene polymer, wherein said material is characterized by a microstructure of voids created by separation of parallel and semi-parallel polymeric chains and has unidirectional high strength and soft and flexible mechanical properties.

2. A nano-porous PTFE biomaterial as described in claim 1 in which the void size is from about 50 nanometers to about 5,000 nanometers.

3. A nano-porous PTFE biomaterial as described in claim 1 in which the density is from about 1.2 gm/cc to about 2.0 gm/cc.

4. A nano-porous PTFE biomaterial as described in claim 1 in which said biomaterial is made of a highly amorphous polytetrafluoroethylene polymer, wherein said material is characterized by a microstructure of voids created by separation of parallel and semi-parallel polymeric chains and layered such that multi-directional strength is attained by orientating the polymeric chains in various relative biases one to another.

5. A nano-porous PTFE biomaterial as described in claim 4 in which the void size is from about 50 nanometers to about 5,000 nanometers.

6. A nano-porous PTFE biomaterial as described in claim 4 in which the density is from about 1.2 gm/cc to about 2.0 gm/cc.

* * * * *